(12) United States Patent
Miles

(10) Patent No.: US 12,419,835 B2
(45) Date of Patent: *Sep. 23, 2025

(54) SYSTEM AND METHOD FOR MAKING CANNABINOID NANOPARTICLE CARRIER COMPOSITION

(71) Applicant: Aaron Miles, McKinleyville, CA (US)

(72) Inventor: Aaron Miles, McKinleyville, CA (US)

(73) Assignee: Aaron Miles, McKinleyville, CA (US)

( * ) Notice: Subject to any disclaimer, the term of this patent is extended or adjusted under 35 U.S.C. 154(b) by 590 days.

This patent is subject to a terminal disclaimer.

(21) Appl. No.: 18/055,282

(22) Filed: Nov. 14, 2022

(65) Prior Publication Data

US 2023/0074245 A1   Mar. 9, 2023

Related U.S. Application Data

(63) Continuation-in-part of application No. 16/946,838, filed on Jul. 8, 2020, now Pat. No. 11,497,727.

(60) Provisional application No. 62/871,653, filed on Jul. 8, 2019.

(51) Int. Cl.
| | | |
|---|---|---|
| *A61K 9/107* | (2006.01) |
| *A61K 31/05* | (2006.01) |
| *A61K 31/352* | (2006.01) |
| *A61K 47/22* | (2006.01) |
| *B01F 23/41* | (2022.01) |
| *B01F 23/411* | (2022.01) |
| *B01F 31/80* | (2022.01) |
| *B01F 101/22* | (2022.01) |

(52) U.S. Cl.
CPC ............ *A61K 9/1075* (2013.01); *A61K 31/05* (2013.01); *A61K 31/352* (2013.01); *A61K 47/22* (2013.01); *B01F 23/4105* (2022.01); *B01F 23/4111* (2022.01); *B01F 23/4143* (2022.01); *B01F 23/4145* (2022.01); *B01F 31/89* (2022.01); *B01F 2101/22* (2022.01)

(58) Field of Classification Search
CPC .................................................. A61K 9/1075
See application file for complete search history.

(56) References Cited

U.S. PATENT DOCUMENTS

| 11,497,727 B2 * | 11/2022 | Miles | ............ A61K 47/26 |
| 12,274,690 B2 * | 4/2025 | Miles | ............ A61K 9/0053 |

\* cited by examiner

*Primary Examiner* — Nizal S Chandrakumar
(74) *Attorney, Agent, or Firm* — Andrew F. Young, ESQ.; NOLTE LACKENBACH SIEGEL

(57) ABSTRACT

A highly stable cannabinoid nanoparticle carrier composition for administration to a human made by incorporating non-ionic surfactants with cannabinoid oils and lipids, sonicating for a predetermined period of time at a predetermined amplification with an ultrasonic liquid processor until completely integrated; combining the mixture with a carrier fluid that includes ascorbic acid and distilled water; and further sonicating the mixture using an ultrasonic liquid processor at predetermined amplitude for a predetermined period of time at a controlled temperature, and thereby to create a CBD nanoemulsion. The composition is tailored using non-ionic surfactants to adsorb to the surface of the cannabinoid oil particles to advantageously affect electrokinetics and surface forces at the interface of the bioactive cannabinoid particles and the suspending liquid are controlled by tailoring the suspending liquid to maximize the zeta potential.

11 Claims, No Drawings

SYSTEM AND METHOD FOR MAKING CANNABINOID NANOPARTICLE CARRIER COMPOSITION

CROSS REFERENCES TO RELATED APPLICATIONS

The present application is a continuation-in-part of U.S. patent application Ser. No. 16/946,838, filed Jul. 8, 2020 (Jul. 8, 2020), which, in turn, claims the benefit of the filing date of U.S. Provisional Patent Application Ser. No. 62/871, 653, filed Jul. 8, 2019 (Jul. 8, 2019), which application is incorporated in its entirety by reference herein.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION BY REFERENCE OF MATERIAL SUBMITTED ON A COMPACT DISC

Not applicable.

BACKGROUND OF THE INVENTION

Field of the Invention: The present invention relates most generally to water soluble emulsions, and more particularly to emulsions containing water-immiscible cannabinoids, and still more particularly to a cannabinoid nanoparticle carrier composition suitable for therapeutic use and having high zeta potential, and thus comprise highly stable nanoemulsions in which the colloids are highly resistant to caking and will, therefore, have high stability and a long shelf life.

Background Discussion: Cannabinoid emulsions are known, as are lipid-based cannabinoid compositions. U.S. Pat. No. 10,028,919, to Kaufman, describes one such composition. And U.S. Pat. App. Ser. No. 2009/01810890, by Kottayil, describes methods for making an effective amount of a cannabinoid in a semi-aqueous solution buffered to a pH of 5-10.

However, each of the above-identified patent publications, while reflecting the current state of the art of which the present inventor is aware, do not teach or disclose, suggest, show, or otherwise render obvious, either singly or when considered in combination, the inventive method described herein. Specifically, the cited references teach cannabinoid products extremely involved manufacturing processes. The present invention, by contrast, is a simple method of formulating a water soluble, lipid-based cannabinoid nanoparticle carrier composition which includes the use of surfactants (i.e., surface active agents or emulsifiers) and sonication or ultrasonic processes to render a highly stable cannabinoid nanoemulsion.

BRIEF SUMMARY OF THE INVENTION

The present invention is a system and method for extracting and making highly stable CBD emulsifications, as well as the product produced thereby.

Because CBD is used both recreationally and medicinally, it is critical that consumable CBD products be amenable to standard product characterization to meet regulatory requirements for labeling and public safety. Dosing to ensure consistent effects (and thus the efficacy and safety) of CBD consumption requires either creating highly stable suspensions or suspensions that can be readily and easily reconstituted after settling or flocculation to have uniform therapeutic particle dispersion and distribution. It is the distinct impression of the present inventor that highly stable suspensions with particles that resist settling and caking are a superior approach to weakly flocculating suspensions when it comes to therapeutically efficacious CBD compositions.

To ensure consistent dosing, the nanoemulsion of the present invention is created with a suspension fluid specially tailored to maintain therapeutic CBD particles in a highly discrete, dispersed, and uniformly suspended state. This is achieved by mixing and then sonicating lipids, non-ionic surfactants, and CBD oils in carefully controlled relative proportions and using timed sonication to produce particle size and dispersion optimal for the product stability, as demonstrated in zeta potential testing and the analysis of various physical properties.

In its most essential aspect, the present invention is a method of producing a cannabinoid nanoparticle carrier composition for administration to a human, including the steps of: (a) mixing non-ionic surfactants with cannabinoid oils and lipids in a mixing vessel; (b) processing the mixture made in step (a) using sonication for a predetermined time at a predetermined amplification until completely processed and substantially all of the cannabinoid oils are reduced to nanoparticle size in a cannabinoid oil complex (COC); (c) dissolving an acid in a carrier fluid to make an acidic carrier fluid solution; (d) mixing the COC made in steps (a) and (b) with the acidic carrier fluid solution made in step (c); and (e) sonicating the mixture made in step (d) using an ultrasonic liquid processor operated at a predetermined amplitude for a predetermined time at a controlled temperature.

In embodiments, the foregoing method may include a first mixing step involving mixing non-ionic surfactants with cannabinoid oils and lipids in relative proportions of between approximately 8:6:3 to approximately 10:9:4 by weight.

In still further embodiments, the first sonication step includes inducing sonication for approximately 40-50 minutes at 60% amplification.

Still other embodiments include sonication using an ultrasonic liquid processor.

Other embodiments can include making an acidic carrier fluid solution consisting of distilled water and ascorbic acid.

In embodiments, the second sonication step can include sonicating at 60% using ultrasonic liquid processor. This embodiment may further include sonicating at 60% amplitude, and still further it may include continuing the sonication a predetermined time, e.g., approximately 5 minutes at a constant temperature, e.g., 24 C.

As will be appreciated from the foregoing, in each of the embodiments above, the method of the present invention produces a cannabinoid-containing nanoparticle carrier composition.

To achieve optimal physical characteristics and product stability, as noted above, the electrokinetics and surface forces at the interface of the bioactive cannabinoid particles and the suspending liquid are controlled by tailoring the suspending liquid to maximize the zeta potential. Non-ionic surfactants, in particular, are employed to adsorb to the surface of the cannabinoid oil particles to shape their electrokinetic characteristics favorably. Testing has shown that the above-described nanoemulsion exhibits remarkable zeta potential characteristics with repulsion measured at magnitudes greater than 39.0 mV (measured potential −39.0 mV or lower), ensuring both stable uniform distribution throughout the emulsion (high homogeneity) and increased solubility, which promotes label accuracy, ensures consistent user experiences, and maximizes product stability.

The detailed description of the invention will provide formulas and methods of combining surfactant and lipid composition ingredients to tailor the charge of the CBD colloids and thereby to create a highly stable CBD nanoemulsion having an optimal zeta potential for product stability and other desirable properties.

DETAILED DESCRIPTION OF THE INVENTION

The present invention is directed to a method of producing a cannabinoid nanoparticle carrier composition for therapeutic use, wherein the cannabinoid carrier composition improves bioavailabilty of the cannabinoids in the composition, as well as improves accurate dosing, due to the more precise measure. Various means of administration may be employed, including intraoral administration, peroral administration, transdermal administration, or intranasal administration.

As will be seen in the following description, the nanoemulsion of the present invention is created with a suspension fluid specially tailored to ensure that the CBD particles are sized and have repulsive surface charges that keep the particles in a discrete state and uniformly suspended for a long product lifetime. The uniformly suspended state has been confirmed by zeta potential tests, known to show improved suspension stability.

An exemplary composition produced by the inventive method may contain:

(1) Firstly, approximately 21-45%, or more precisely, 21.05-45.70% cannabinoids comprising at least one of the Phytocannabinoids found in cannabis that include delta Tetrahydrocannabinol (THC), Cannabidiol (CBD), Cannabinol (CBN) Cannabigerol (CBG}, Cannabigerol {CBG), Cannabichromene (CBC), Cannabicyclol (CBL), Canabivarol (CBV), Tetrahydrocannabiverin (THCV), Cannabidivarin (CBDV), Cannabichromevarin (CBCV, Cannabigerol Monoethyi ether (CBGM);

(2) secondly, 7-20%, or more precisely, 7.14-20.18% lipids (medium chain triglycerides, glycerides, hemps seed oil, safflower oil, sunflower oil, olive oil, etc.); and (3) thirdly, 40-50%, or more precisely, 38.6-49.42% pharmaceutical food grade surfactants, generally comprising a combination of lipophilic Span and Tween-hydrophilic, the latter sold as Tween 80 (polysorbate 80), E433, to function as emulsifiers. The surfactant emulsifiers may be used independently or in combination, with available options including: 20, sorbitan monopalmitate; Span® 40, sorbitan monopalmitate; Span® 60, sorbitan monostearate; and Span 80, sorbitan monooleate). Tween® surfactants are hydrophilic, Span® surfactants are lipophilic. Testing has shown the optimal combinations to include TWEEN 80 at 17.0-21.61% and/or Span 80 at 21.6-27.81%. [TWEEN is a registered trademark of Croda Americas LLC of Bridgewater, New Jersey; SPAN is a registered trademark of Merck KGaA of Darmstadt, Germany.]

Depending on the desired nanoemulsion properties, the remainder of the composition may include distilled water and, optionally, ascorbic acid, in a combined amount of 0.0% to 76% by weight.

An exemplary non-limiting method of making the inventive composition entails the following steps, wherein the steps are non-limiting in the relative proportions of the composition components and recited amounts are understood to be close approximations:

(1) Mixing non-ionic surfactants with cannabinoid oils, and lipids in a mixing vessel, e.g., a 200 ml beaker, in the range of relative proportions (by weight) set out above.

(2) Inducing sonication for 40-50 minutes at 60% amplification with a ultrasonic liquid processor until completely integrated.

(3) If an acid carrier fluid is to be used, dissolving ascorbic acid into a carrier fluid selected from the group consisting of distilled water, glycerides, lipids, or a mixture thereof.

(4) Thus, optionally, combining in sequence the non-ionic surfactants, lipids, and cannabanoid oil complex (COC) with the carrier fluid/ascorbic acid solution.

(5) Sonicating at 60% using ultrasonic liquid processor at 60% amplitude for 5 minutes, at a constant 24c temperature.

The following protocol applies: The ingredients are processed using a single or dual phase process utilizing sonication or ultrasonic processes for a determined period of time to produce a lipid-based, water-soluble nanoemulsion.

The formula consists of: (a) non-ionic TWEEN® or SPAN® pharmaceutical food grade surfactants, alone or together in specific combinations and percentages, to acquire approximately (+/−2% for each component): 17% to 50% total surfactants by weight; (b) a lipid, preferably refined olive oil, 7% to 20% by weight; (c) ascorbic acid 0.00% to 1.0% by weight; (d) THC or CBD cannabinoids in any form of hemp or any classification form in any combination, whether concentration quantity or potency, 21% to 45% by weight, in specific combinations; and (e) depending on the foregoing proportional amounts, to achieve 100% of total formula weight or volume, the remaining ingredient is distilled water alone.

Using the above-described steps for mixing the composition ingredients, exemplary embodiments with discrete ingredients within the optimal ranges include the following (set out in relative percentages by weight):

Lipids (e.g., olive oil 7.24; ascorbic acid 1.0; water 53.0; Span 80, 9.92; Tween 80 7.79; and CBD 21.05.

In an alternative exemplary embodiment, the composition may include: lipids (e.g., olive oil 20.18; Span 80, 27.81; Tween 80 21.61; and CBD 30.40.

In yet another exemplary embodiment, the composition may include: lipids (e.g., olive oil 15.7; Span 80, 21.6; Tween 80, 17.0, and CBD 45.7.

Zeta potentials (surface charges) of the nanostructure lipid carriers (NLPs) stabilized in the non-ionic surfactants for all of the above-described compositions, as precisely set out, exceed magnitudes of −39.0 mV and range to −61.9 mV, indicating very high stabilization of the nanoemulsions. The mean hydrodynamic particle diameter of the NLPs ranged between 206 and 639 nm.

Importantly, while achieving the desired physical characteristics described, the inventive composition does not include lecithin or lecithin-based essential phospholipids. Rather, the nanoemulsion is achieved through the application of sonication or ultrasonic processing to the lipid/surfactant/CBD oil water-immiscible mixture.

The above disclosure is sufficient to enable one of ordinary skill in the art to practice the invention and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the claims included herein.

What is claimed as invention is:

1. A method of producing a cannabinoid nanoparticle carrier composition for administration to a human, comprising:
   (a) mixing non-ionic surfactants with cannabinoid oils and lipids in a mixing vessel in relative proportions to achieve an approximate 17% to 50% by weight of total surfactants, 7% to 20% by weight of lipids, 0.0% to 1.0% by weight of ascorbic acid, 21% to 45% by weight of THC or CBD cannabinoids in any form of hemp or any classification form in any combination, whether concentration quantity or potency, and 0% to 53% distilled water, the ingredients in specific combinations to achieve 100% of total formula weight or volume, +/−2% for each component;
   (b) processing the mixture made in step (a) using sonication until completely processed and substantially all of the cannabinoid oils are reduced to nanoparticle size in a cannabinoid oil complex (COC);
   (c) dissolving an acid in a carrier fluid to make an acidic carrier fluid solution;
   (d) mixing the COC made in steps (a) and (b) with the acidic carrier fluid solution made in step (c); and
   (e) sonicating the mixture made in step (d) using an ultrasonic liquid processor.

2. The method of claim 1 wherein said step (a) mixing step comprises mixing approximately 18% of non-ionic surfactants with approximately 21% cannabinoid oils, and approximately 7% lipids.

3. The method of claim 1 wherein said step (a) mixing step comprises mixing approximately 49% of non-ionic surfactants with approximately 30% cannabinoid oils, and approximately 20% lipids.

4. The method of claim 1 wherein said step (a) mixing step comprises mixing approximately 39% of non-ionic surfactants with approximately 46% cannabinoid oils, and approximately 16% lipids.

5. The method of claim 1, wherein said step (b) processing step comprises inducing sonication for approximately 40-50 seconds at 60% amplification.

6. The method of claim 5, wherein said step (b) processing step involves using an ultrasonic liquid processor.

7. The method of claim 5, wherein said carrier fluid is selected from the group consisting of distilled water, glycerides, and lipids, and mixtures thereof.

8. The method of claim 1, wherein the acidic carrier fluid solution comprises approximately 53% distilled water and approximately 1% ascorbic acid.

9. The method of claim 8, wherein step (e) involves sonicating at 60% amplitude using ultrasonic liquid processor.

10. The method of claim 9, wherein the sonication of step (e) is continued for approximately 5 minutes.

11. The method of claim 10, wherein the sonication is carried out at a constant 24° C. temperature.

* * * * *